US012728290B2

(12) United States Patent
Kim et al.

(10) Patent No.: US 12,728,290 B2
(45) Date of Patent: Sep. 8, 2026

(54) ULTRASONIC WAVE GENERATING APPARATUS CAPABLE OF ADJUSTING FOCUSING DEPTH OF ULTRASONIC WAVES

(71) Applicant: JEISYS MEDICAL INC., Seoul (KR)

(72) Inventors: Kyuntae Kim, Seoul (KR); Won Ju Yi, Seoul (KR); Dong Hwan Kang, Seoul (KR)

(73) Assignee: JEISYS MEDICAL INC., Seoul (KR)

( * ) Notice: Subject to any disclaimer, the term of this patent is extended or adjusted under 35 U.S.C. 154(b) by 60 days.

(21) Appl. No.: 18/491,542

(22) Filed: Oct. 20, 2023

(65) Prior Publication Data

US 2024/0042243 A1 Feb. 8, 2024

Related U.S. Application Data

(63) Continuation of application No. PCT/KR2022/005703, filed on Apr. 21, 2022.

(30) Foreign Application Priority Data

May 13, 2021 (KR) ........................ 10-2021-0061909

(51) Int. Cl.
*A61N 7/00* (2006.01)

(52) U.S. Cl.
CPC ........ *A61N 7/00* (2013.01); *A61N 2007/0034* (2013.01); *A61N 2007/0091* (2013.01)

(58) Field of Classification Search
CPC .............. A61N 7/00; A61N 2007/0034; A61N 2007/0091; A61N 7/02; A61N 2007/0056; A61N 2007/025
See application file for complete search history.

(56) References Cited

U.S. PATENT DOCUMENTS 4,065,976 A * 1/1978 Taenzer ................. G01N 29/06 74/25
4,494,548 A * 1/1985 Buon .................. G10K 11/355 73/620

(Continued)

FOREIGN PATENT DOCUMENTS

EP 3922308 A1 12/2021
KR 101307551 B1 9/2013

(Continued)

OTHER PUBLICATIONS

Machine translation of KR-101335476-B1.*

(Continued)

*Primary Examiner* — Oommen Jacob

(57) ABSTRACT

Disclosed is an ultrasonic wave generating apparatus capable of adjusting a focusing depth of ultrasonic waves including a handpiece, a cartridge housing, an ultrasonic wave generating unit provided in the cartridge housing, connected to a movable shaft extending from the handpiece, and including a transducer that generates ultrasonic waves, a variable shaft connected to the ultrasonic wave generating unit and that is movable in an upward/downward direction of the transducer, and a manipulation part that moves the variable shaft in the upward/downward direction. The movable shaft is configured to be movable in an axial direction of the variable shaft. The ultrasonic wave generating apparatus may be moved in the upward/downward direction through manipulation of the manipulation part to be moved in the axial direction of the variable shaft after a target location in the upward/downward direction is determined.

18 Claims, 8 Drawing Sheets

(56) References Cited

U.S. PATENT DOCUMENTS 4,785,819 A * 11/1988 Pearce ................. G10K 11/355 600/446
8,573,392 B2 * 11/2013 Bennett ............. B65D 81/2076 600/436
10,363,440 B2 7/2019 Cho et al.
10,537,304 B2 * 1/2020 Barthe ................... A61B 8/467
10,856,842 B2 12/2020 Park et al.
12,257,460 B2 * 3/2025 Park ......................... A61N 7/02
2002/0055702 A1 * 5/2002 Atala ................ A61M 37/0092 600/38
2008/0027328 A1 * 1/2008 Klopotek ............. A61B 8/4281 600/472
2011/0077514 A1 * 3/2011 Ulric .................... A61B 8/4405 600/439
2015/0321026 A1 * 11/2015 Branson ................... A61N 7/00 601/2
2016/0001097 A1 * 1/2016 Cho ......................... A61B 8/44 601/3
2016/0175619 A1 * 6/2016 Lee ........................ A61N 7/022 601/3
2017/0303888 A1 * 10/2017 Jung ........................ A61B 8/42
2017/0303895 A1 10/2017 Park et al.
2018/0353778 A1 * 12/2018 Jeong ....................... A61N 7/00
2019/0134430 A1 * 5/2019 Jeong ....................... A61N 7/02
2019/0366129 A1 * 12/2019 Park ......................... A61N 7/02
2021/0387023 A1 * 12/2021 Kim ......................... A61N 7/02
2023/0310902 A1 * 10/2023 Kim ......................... A61N 7/00
2023/0321461 A1 10/2023 Jung et al.
2024/0065676 A1 2/2024 Kim et al.

FOREIGN PATENT DOCUMENTS

KR 101335476 B1 * 12/2013 ............... A61N 7/02
KR 101623528 B1 5/2016
KR 101687569 B1 * 12/2016 ............... A61N 7/02
KR 10-2017-0074716 A 6/2017
KR 10-2018-0015095 A 2/2018
KR 20180015095 A * 2/2018 ............... A61N 7/02
KR 10-1893584 B1 8/2018
KR 10-2020-0006861 A 1/2020
WO WO 2022158677 A1 7/2022
WO WO 2022231274 A1 11/2022

OTHER PUBLICATIONS

Machine translation of KR-101687569-B1.*
Machine translation of KR-20180015095-A.*
European Search Report regarding Application No. 22807643.6, Jul. 15, 2024.
International Search Report issued in PCT/KR2022/005703; mailed Jul. 25, 2022.
Korean Patent Office, Notice of Submission of Opinions regarding Application No. 10-2023-0136331, Jun. 2, 2024.

* cited by examiner

ULTRASONIC WAVE GENERATING APPARATUS CAPABLE OF ADJUSTING FOCUSING DEPTH OF ULTRASONIC WAVES

CROSS-REFERENCE TO RELATED APPLICATIONS

The present application is a continuation of International Patent Application No. PCT/KR2022/005703, filed on Apr. 21, 2022, which is based upon and claims the benefit of priority to Korean Patent Application No. 10-2021-0061909 filed on May 13, 2021. The disclosures of the above-listed applications are hereby incorporated by reference herein in their entirety.

BACKGROUND

Embodiments of the inventive concept described herein relate to an ultrasonic wave generating apparatus capable of adjusting a focusing depth of ultrasonic waves.

Ultrasonic waves refer to waves having a frequency of 20 kHz or higher, and are widely used in the medical field for diagnosis and treatment of affected areas as well as for skin care.

In particular, high intensity focused ultrasounds (HIFUs), a high-intensity focused form of ultrasounds, may be non-invasively focused at a target depth of skin while not damaging the surface of the skin, unlike laser and radio frequency (RF) high-frequency waves. As a result, while a rapid temperature increase is induced at the target depth of the skin, coagulative necrosis of cells occurs without leaving side effects on various affected parts of the skin. These necrotic cells are naturally removed by the body's mechanism for repairing damaged parts.

Meanwhile, a conventional ultrasonic wave generating apparatus has a cartridge housing and an ultrasonic wave generating unit embedded in the cartridge housing to irradiate ultrasonic waves.

According to the conventional ultrasonic wave generating apparatus, because the ultrasonic wave generating unit is fixed inside the cartridge housing, it is difficult to adjust a focusing depth of the ultrasonic waves of the ultrasonic wave generating unit.

Accordingly, the existing ultrasonic wave generating apparatus cannot adjust a focusing depth of ultrasonic waves according to a target depth of skin.

SUMMARY

Embodiments of the inventive concept provide an ultrasonic wave generating apparatus that may easily adjust a focusing depth of ultrasonic waves according to a target depth of skin.

The problems to be solved by the inventive concept are not limited to the above-mentioned ones, and the unmentioned problems will be clearly understood by an ordinary person in the art from the following description.

According to an embodiment, an ultrasonic wave generating apparatus capable of adjusting a focusing depth of ultrasonic waves includes a handpiece, a cartridge housing, an ultrasonic wave generating unit provided in the cartridge housing, connected to a movable shaft extending from the handpiece, and including a transducer that generates ultrasonic waves, a variable shaft connected to the ultrasonic wave generating unit and that is movable in an upward/downward direction of the transducer, and a manipulation part that moves the variable shaft in the upward/downward direction, the movable shaft is configured to be movable in an axial direction of the variable shaft.

According to an embodiment, the variable shaft may be configured to be expanded and contracted in the axial direction of the variable shaft by the movable shaft.

According to an embodiment, the variable shaft may include one or more shafts having different diameters and that is inserted and extracted in multi-stage.

According to an embodiment, the ultrasonic wave generating apparatus may include a guide part provided in the cartridge housing, and that guides the ultrasonic wave generating unit such that the ultrasonic wave generating unit is movable in the upward/downward direction and the axial direction of the variable shaft, and the guide part may include a guide shaft passing through the ultrasonic wave generating unit.

According to an embodiment, the guide part may further include one or more elastic members provided in the ultrasonic wave generating unit.

According to an embodiment, the ultrasonic wave generating apparatus may further include a first magnetic member provided in the ultrasonic wave generating unit, and a second magnetic member provided in the movable shaft and magnetically coupled to the first magnetic member.

According to an embodiment, the manipulation part may be a driver, a button, or a knob.

Other detailed items of the inventive concept are included in the detailed description and the drawings.

BRIEF DESCRIPTION OF THE FIGURES

The above and other objects and features will become apparent from the following description with reference to the following figures, wherein like reference numerals refer to like parts throughout the various figures unless otherwise specified, and wherein.

DETAILED DESCRIPTION

Figure 1:
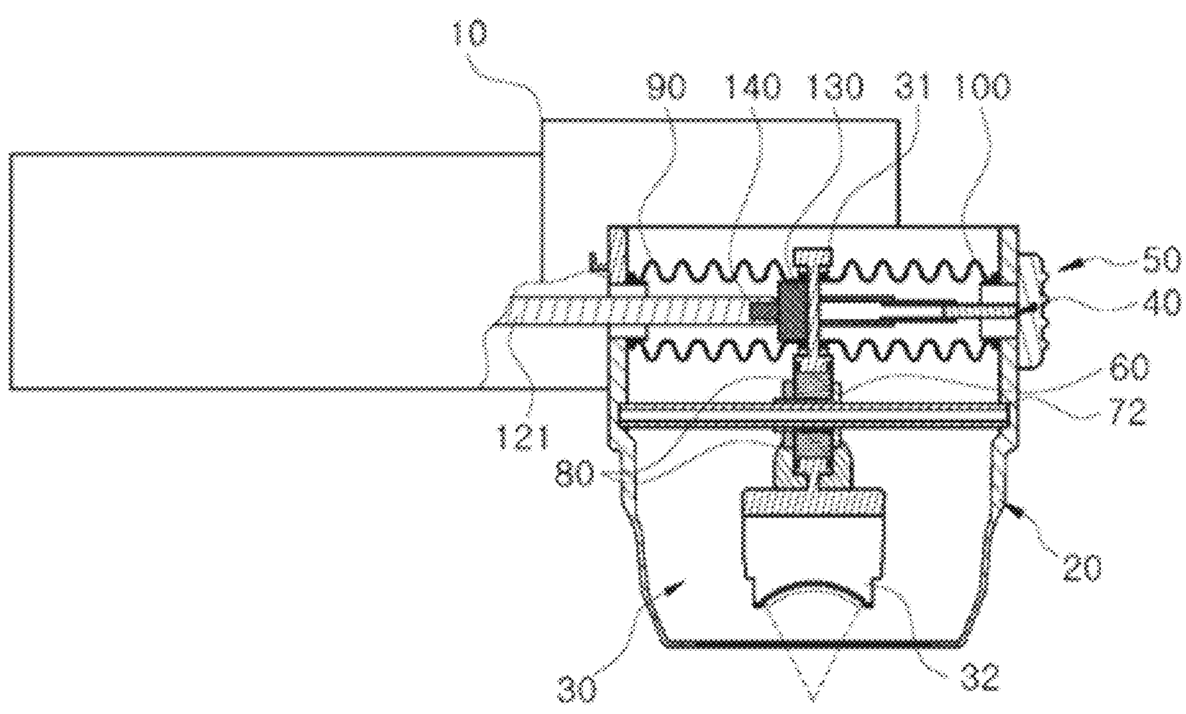
FIG. 1 is a schematic view illustrating an ultrasonic wave generating apparatus according to a first embodiment of the inventive concept.

The advantages and the features of the inventive concept, and the method for achieving them will become apparent from the following description of the embodiments, which will be described below in detail, together with the accompanying drawings. However, the inventive concept is not limited by the embodiments disclosed below and may be implemented in various different forms, and the embodiments are simply provided to make the disclosure of the inventive concept complete and to fully inform an ordinary person in the art, to which the inventive concept pertains, of the scope of the inventive concept, and the inventive concept is defined only by the scope of the claims.

The terms used in the specification is for explaining the embodiments, and are not intended to limit the inventive concept. A singular expression includes a plural expression unless an exemption is explicitly described in the context. The terms "comprises" and/or "comprising" used herein does not exclude presence or addition of one or more other elements, in addition to the aforementioned elements. Throughout the specification, the same reference numerals denote the same elements, and "and/or" includes the respective elements and all combinations of the elements. Although "first", "second" and the like are used to describe various elements, the elements are not limited by the terms. The terms are used simply to distinguish one element from other elements. Accordingly, it is apparent that a first element mentioned in the following may be a second element without departing from the spirit of the inventive concept.

Unless otherwise defined, all terms (including technical and scientific terms) used herein have the same meaning as commonly understood by those skilled in the art to which the inventive concept pertains. Furthermore, the terms defined in commonly used dictionaries should not be interpreted in an idealized or overly formal sense unless expressly so defined herein.

Hereinafter, embodiments of the inventive concept will be described in detail with reference to the accompanying drawings.

Prior to a description of the inventive concept, in several embodiments, a first embodiment will be representatively described while the same reference numerals are used for the elements having the same configurations, and in the other embodiments, other configurations than those of the first embodiment will be described.

Figure 2:
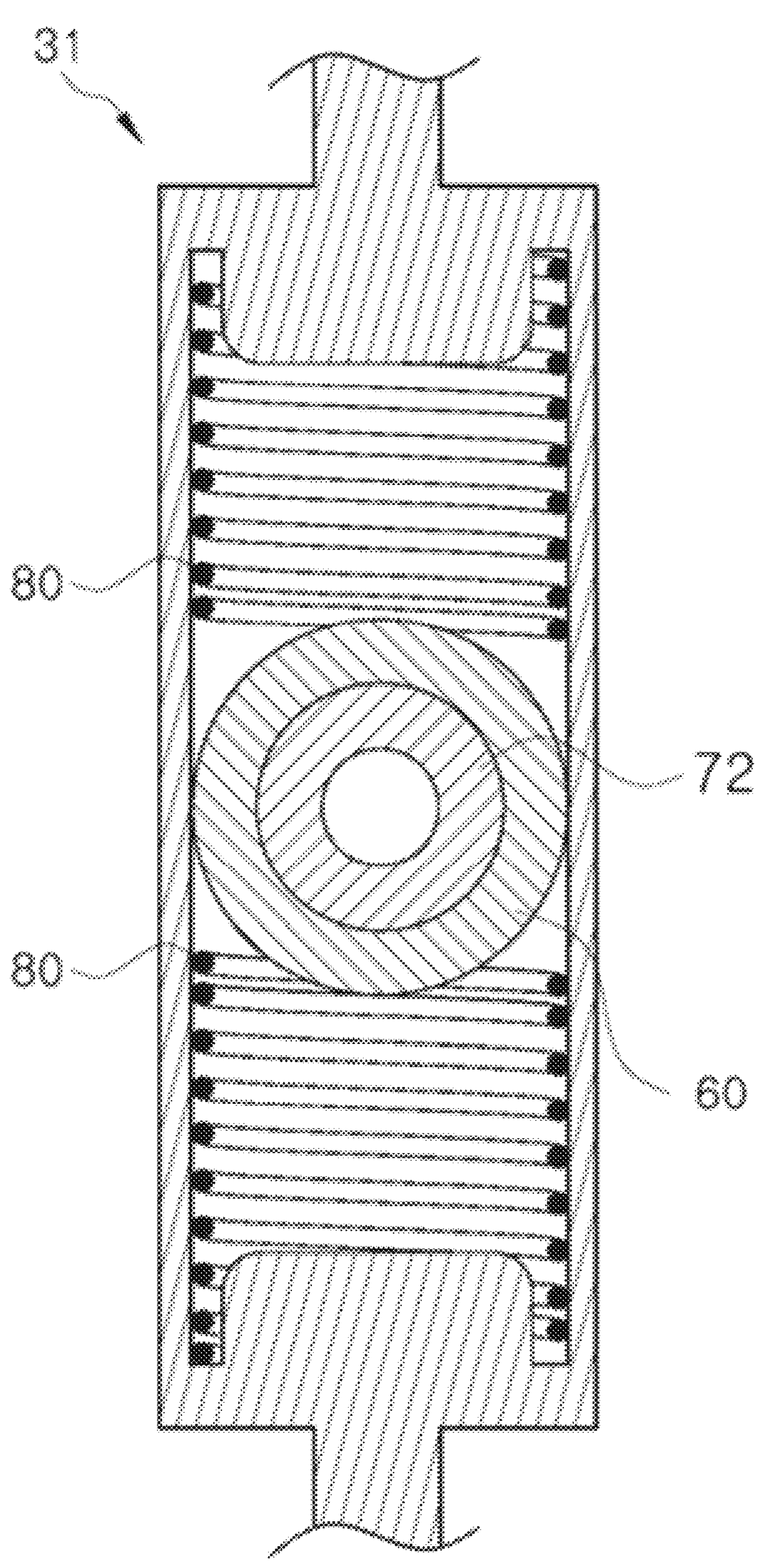
FIG. 2 is a cross-sectional view illustrating a connector of the ultrasonic wave generating apparatus according to the first embodiment of the inventive concept.

FIG. 1 is a schematic view illustrating an ultrasonic wave generating apparatus according to a first embodiment of the inventive concept, and FIG. 2 is a cross-sectional view illustrating a connector of the ultrasonic wave generating apparatus according to the first embodiment of the inventive concept.

As illustrated in FIG. 1, the ultrasonic wave generating apparatus according to the first embodiment of the inventive concept includes a handpiece 10, a cartridge housing 20, an ultrasonic wave generating unit 30, a variable shaft 40, a manipulation part 50, and a guide part.

Here, the handpiece 10 and the cartridge housing 20 correspond to a basic body, the ultrasonic wave generating unit 30 includes a transducer 32 that generates ultrasonic waves, the variable shaft 40 and the manipulation part 50 function to move the ultrasonic wave generating unit 30 in an upward/downward direction of the transducer 32, and the guide part is provided in the cartridge housing 20 to function to guide the ultrasonic wave generating unit 30 such that the ultrasonic wave generating unit 30 may be moved in the upward/downward direction of the transducer 32 and an axial direction of the variable shaft 40.

The handpiece 10 is a basic body, and may be utilized as a gripper for gripping of a user, and the cartridge housing 20, which will be described below, is detachably coupled to one side of the handpiece 10. The ultrasonic wave generating unit 30 having the transducer 32 that generates ultrasonic waves is disposed in an interior of the cartridge housing 20. Accordingly, in a state in which the user grips the handpiece 10 and moves the handpiece 10 such that the cartridge housing 20 comes into close contact with the surface of skin, an ultrasonic medical surgery may be carried out by irradiating the ultrasonic waves generated by the transducer 32 to a target depth of the skin.

A cable connected to an RF board for applying an RF current to the transducer 32 may be provided in an interior of the handpiece 10. The RF board may be accommodated in a main body or the handpiece 10, and may intermittently or continuously apply RF currents to the transducer 32.

The cartridge housing 20 is a kind of case that accommodates the transducer 32, and is detachably coupled to the handpiece 10.

A fluid medium for delivering ultrasonic waves generated by the transducer 32 may be accommodated in the cartridge housing 20. Here, the fluid medium may be distilled water, degassing liquid, or silicon, but the inventive concept is not particularly limited thereto.

The ultrasonic wave generating unit 30 is provided in the cartridge housing 20, and includes a connector 31 that is connected to the variable shaft 40, which will be described below, and the transducer 32 that is connected to the connector 31 and generates ultrasonic waves.

The connector 31 is provided in the cartridge housing 20, and one side of the connector 31 is connected to the variable shaft 40 and an opposite side of the connector 31 is connected to the transducer 32.

The transducer 32 may receive an electrical signal from the RF board by using the cable of the handpiece 10, and may focus the ultrasonic waves to a specific location. Here, the upward/downward direction of the transducer 32 may be defined as a direction, in which the focusing depth of the ultrasonic waves of the transducer 32 is changed.

Here, a vertical distance from a distal end of the cartridge housing 20 to the specific location, at which the ultrasonic waves are focused, may be defined as the focusing depth of the ultrasonic waves of the transducer 32. In the embodiment, the focusing depth of the ultrasonic waves of the transducer 32 may be adjusted as the ultrasonic wave generating unit 30 is moved in the upward/downward direction of the transducer 32, and this will be described below.

Meanwhile, the ultrasonic wave generating unit 30 may be detachably coupled to the cartridge housing 20. For example, the ultrasonic wave generating unit 30 may be screw-coupled to the cartridge housing 20. Furthermore, the ultrasonic wave generating unit 30 may be located in the cartridge housing 20, and as an example, may be detachably coupled thereto through a boss and a recess.

The guide part may include a guide shaft 72 that passes through the ultrasonic wave generating unit 30.

Referring to FIG. 2, one or more elastic members 80 that elastically support the guide shaft 72, which will be described below, may be provided in the connector 31 of the ultrasonic wave generating unit 30.

The guide shaft 72 guides movement of the transducer 32 in the upward/downward direction, and movement of the variable shaft 40 in the axial direction. As will be described below, a movable shaft 121 functions to move the ultrasonic wave generating unit 30 in the axial direction of the variable shaft 40.

The guide shaft 72 may be provided in the cartridge housing 20 to be disposed in parallel to the variable shaft 40, and the connector 31 may be coupled to be movable in the upward/downward direction of the transducer 32. The guide shaft 72 may be fixed to the cartridge housing 20, and for example, opposite surfaces of the guide shaft 72 may be coupled to opposite surfaces of the cartridge housing 20.

Meanwhile, the guide shaft 72 may be coupled to the connector 31 of the ultrasonic wave generating unit 30 to be slid.

Furthermore, the guide shaft 72 may be disposed on a lower side of the variable shaft 40.

As described above, because the connector 31 of the ultrasonic wave generating unit 30 is coupled to the guide shaft 72 to be slid, the ultrasonic wave generating unit 30 may be prevented from being pivoted while the in the upward/downward direction moving in the upward/downward direction of the transducer 32 or moving in the axial direction of the variable shaft 40 when the location of the ultrasonic wave generating unit 30 is adjusted whereby an ultrasonic wave treatment may be stably performed through the transducer 32 of the ultrasonic wave generating unit 30 while the location of the ultrasonic wave generating unit 30 is precisely adjusted.

One or more elastic members 80 may be provided in an interior of the connector 31 of the ultrasonic wave generating unit 30.

The one or more elastic members 80 may elastically support the guide shaft 72. In detail, a pair of elastic members 80 may be provided, and the pair of elastic members 80 may be disposed to face each other in the upward/downward direction while a bushing 60, on which the guide shaft 72 is slid, being interposed therebetween to elastically support the bushing 60 that is inserted into the interior of the connector 31 of the ultrasonic wave generating unit 30. Springs may be used for the elastic members 80, but the inventive concept is not particularly limited thereto.

The bushing 60 surrounds a specific portion of the guide shaft 72. The bushing 60 may be slid in the axial direction of the guide shaft 72, and the connector 31 also may be slid along the in the axial direction of the guide shaft 72 in conjunction therewith. Meanwhile, the pair of elastic members 80 may be disposed to face each other in the upward/downward direction while the bushing 60 being interposed therebetween, and may elastically support the bushing 60.

Here, in the embodiment, although the bushing 60 is coupled to the guide shaft 72 to be slid and the bushing 60 is elastically supported by the pair of elastic members 80, the inventive concept is not limited thereto and the bushing 60 may be optionally provided. In this case, the connector 31 may be moved in the axial direction of the guide shaft 72, and the guide shaft 72 may be elastically supported by the pair of elastic members 80.

The variable shaft 40 is coupled to the ultrasonic wave generating unit 30, and is disposed in parallel to the upward/downward direction of the transducer 32. In detail, the variable shaft 40 may be connected to the connector 31 of the ultrasonic wave generating unit 30. Accordingly, when the variable shaft 40 is moved in the upward/downward direction of the transducer 32, the ultrasonic wave generating unit 30 may also be moved in the upward/downward direction of the transducer 32 in conjunction therewith.

Opposite ends of the variable shaft 40 may be coupled to the manipulation part 50, which will be described below, and the connector 31.

The variable shaft 40 may be disposed in parallel to a direction that is perpendicular to the upward/downward direction of the transducer 32. Here, the direction that is perpendicular to the upward/downward direction of the transducer 32 may be the axial direction of the variable shaft 40.

The variable shaft 40 may be configured to be expanded and contracted in the axial direction of the variable shaft 40 by the movable shaft 121. Meanwhile, when the variable shaft 40 is expanded and contracted, the connector 31 may be moved in the axial direction of the variable shaft 40.

The variable shaft 40 may include one or more shafts that have different diameters and may be inserted and extracted in multi-stage. In other words, the variable shaft 40 may have a form, in which a plurality of shafts having different diameters are coupled to each other in a telescopic manner.

The manipulation part 50 is coupled to the variable shaft 40, and moves the variable shaft 40 along the upward/downward direction of the transducer 32. When the variable shaft 40 is moved in the upward/downward direction of the transducer 32 by the manipulation part 50, the ultrasonic wave generating unit 30 also may be moved in the upward/downward direction of the transducer 32 in conjunction therewith whereby a focusing depth of the ultrasonic waves of the transducer 32 may be easily adjusted.

As an example, the manipulation part 50 may be a driving means that drives the variable shaft 40 in the upward/downward direction of the transducer 32.

As another example, the manipulation part 50 may be a knob that is coupled to a distal end of the variable shaft 40. A force for moving the knob in the upward/downward direction of the transducer 32 may be applied to the knob by the user. Here, the manipulation part 50 may be moved along a rack gear having a specific length, in the upward/downward direction, on an outer surface of the cartridge housing 20. Furthermore, a pinion gear that is selectively stopped or released from the rack gear may be provided in the manipulation part 50.

The movable shaft 121 functions to move the transducer 32 in the axial direction of the variable shaft 40. The movable shaft 121 may be configured to be moved in the axial direction of the variable shaft.

The movable shaft 121 may be coupled to the variable shaft 40, and may move the connector 31 coupled to the variable shaft 40 in the axial direction of the variable shaft 40 by expanding and contracting the variable shaft 40. Here, the movable shaft 121 may be moved in the axial direction of the variable shaft 40 to expand and contract the variable shaft 40. The movable shaft 121 may be moved by a driving device. Here, the driving device may be an actuator and a driving motor, but the inventive concept is not particularly limited thereto.

Meanwhile, the movable shaft 121 and the variable shaft 40 may be coupled to each other to be separable by a first magnetic member 130 and a second magnetic member 140, which will be described below.

The first magnetic member 130 may be provided on the connector 31 while facing the variable shaft 40. The first magnetic member 130 may have a length that is equal to or greater than a maximum movement distance of the variable shaft 40. Here, the maximum movement distance of the variable shaft 40 may be defined as a distance, by which the variable shaft 40 may be maximally moved from the cartridge housing 20 with respect to the upward/downward direction of the transducer 32.

The second magnetic member 140 may be provided on the movable shaft 121 to be magnetically coupled to the first magnetic member 130. The second magnetic member 140 may have a length that is smaller than that of the first magnetic member 130 with respect to the upward/downward direction of the transducer 32.

Meanwhile, a first tube 90 that accommodates one area of the movable shaft 121, and the first magnetic member 130 and the second magnetic member 140 may be provided between one surface of the cartridge housing 20 and the connector 31. A second tube 100 that accommodates the variable shaft 40 may be provided between an opposite surface of the cartridge housing 20 and the connector 31. The first tube 90 and the second tube 100 may be bellows tubes that may be expanded and contracted.

Furthermore, the first tube 90 and the second tube 100 may have an elliptical shape that has a long axis, of which a length in the upward/downward direction of the transducer 32 is larger than lengths thereof in the other directions. As described above, the first tube 90 and the second tube 100 have the elliptical shape whereby movement ranges of the movable shaft 121 and the variable shaft 40 may be ensured and a sealing performance between the inside and the outside of the cartridge housing 20 may be also ensured when the movable shaft 121 and the variable shaft 40 are moved in the upward/downward direction of the transducer 32.

Furthermore, the first tube 90 and the second tube 100 are formed of a material having soft characteristics, such as urethane or silicon whereby leakage of the medium may be prevented by restraining a possibility of generation of an aperture in the first tube 90 and the second tube 100 and a reliability of the sealing performance may be secured more.

As an example, the ultrasonic wave generating unit 30 may be moved in the upward/downward direction of the transducer 32 through manipulation of the manipulation part 50, and may be moved in the axial direction of the variable shaft 40 by the movable shaft 121 after a target location of the transducer 32 in the upward/downward direction is determined.

Here, when the target location of the transducer 32 in the upward/downward direction with respect to the ultrasonic wave generating unit 30 is determined, the focusing depth of the ultrasonic waves of the transducer 32 may be adjusted to a target depth under skin.

Furthermore, while the ultrasonic wave generating unit 30 is moved in a linear path in the axial direction of the variable shaft 40 by the movable shaft 121, the transducer 32 may be operated whereby the ultrasonic waves generated by the transducer 32 may be provided along the linear path in the axial direction of the variable shaft 40 at the target depth under the skin.

Hereinafter, an example of adjusting a focusing depth of ultrasonic waves of the transducer 32 of the ultrasonic wave generating apparatus according to the first embodiment of the inventive concept will be described.

Figure 3:
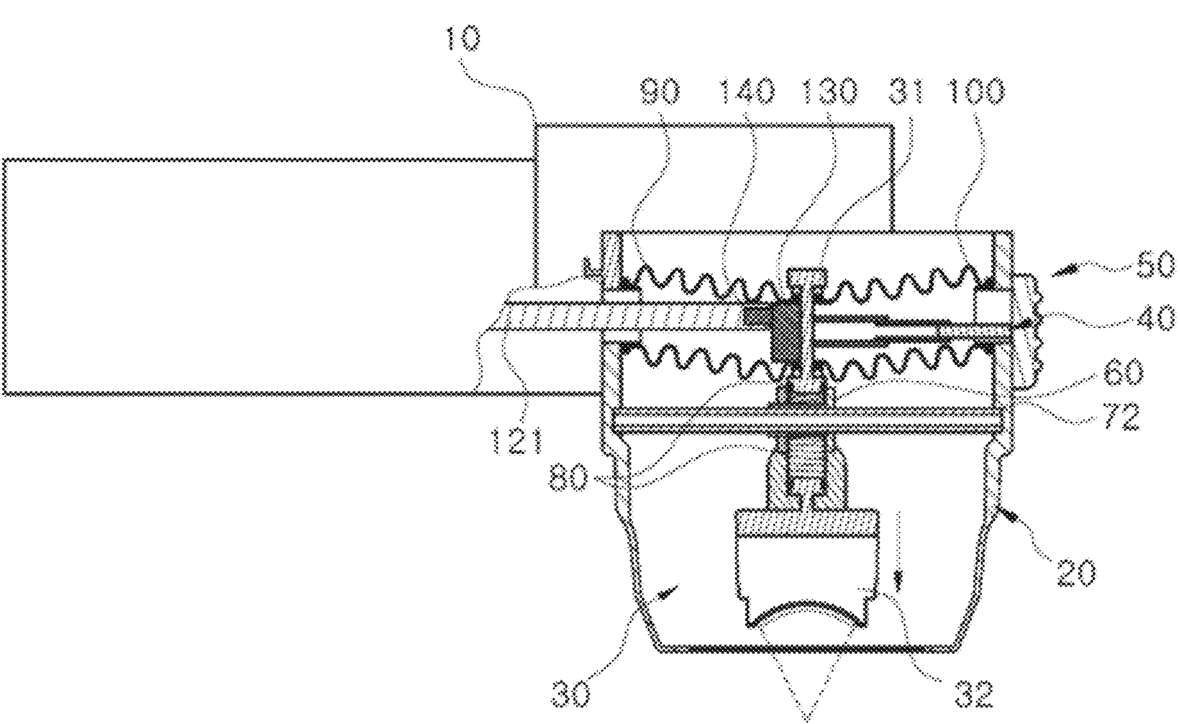
FIGS. 3 and 4 are operation views illustrating states, in which a focusing depth of ultrasonic waves of a transducer of the ultrasonic wave generating apparatus according to the first embodiment of the inventive concept is adjusted.
Figure 4:
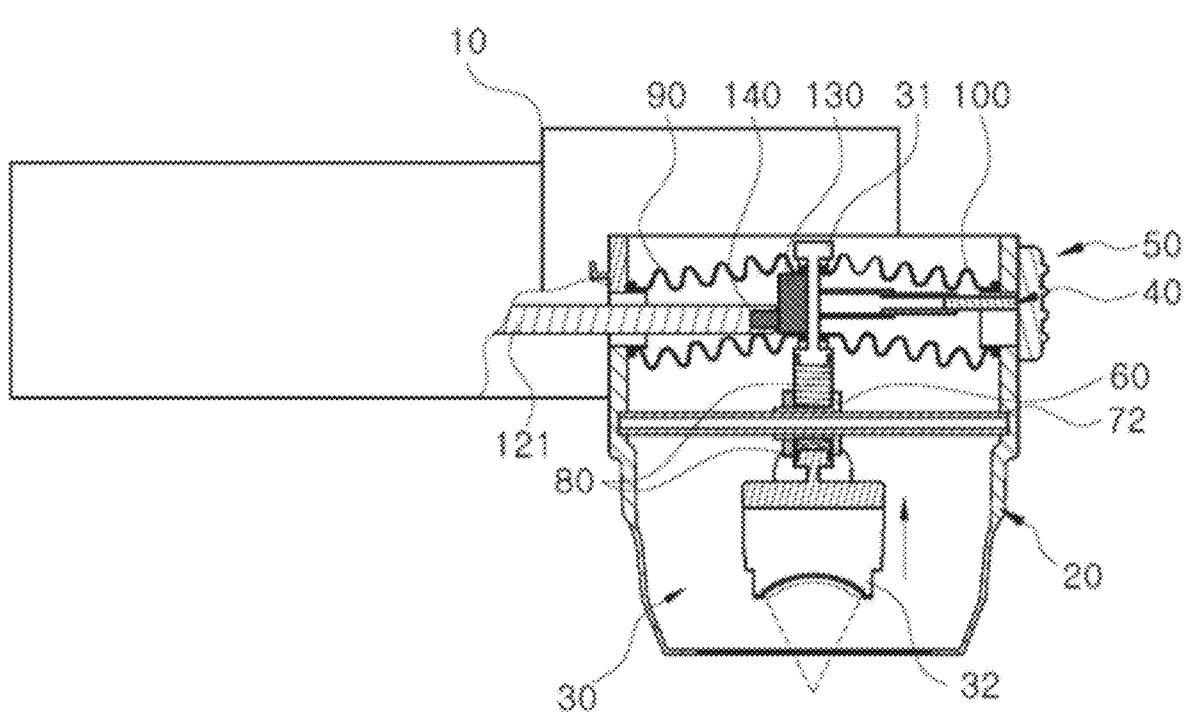

FIGS. 3 and 4 are operation views illustrating states, in which a focusing depth of ultrasonic waves of the transducer of the ultrasonic wave generating apparatus according to the first embodiment of the inventive concept is adjusted.

As illustrated in FIG. 3, first, the manipulation part 50 moves the variable shaft 40 downwards. Then, the manipulation part 50 may be manually moved downwards through manipulation by the user.

Next, the ultrasonic wave generating unit 30 also is moved downwards in conjunction with downward movement of the variable shaft 40. As a result, the focusing depth of the ultrasonic waves of the transducer 32 becomes larger.

Meanwhile, when the variable shaft 40 is moved downwardly, the movable shaft 121 is fixed but the variable shaft 40 is moved downwardly. Accordingly, the second magnetic member 140 may be coupled to an upper side of the first magnetic member 130 while the first magnetic member 130 provided on the variable shaft 40 is moved downwardly.

Furthermore, when the ultrasonic wave generating unit 30 is moved downwards, the pair of elastic members 80 elastically support the ultrasonic wave generating unit 30 whereby the ultrasonic wave generating unit 30 may be prevented from being pivoted.

Subsequently, as illustrated in FIG. 4, the manipulation part 50 moves the variable shaft 40 upwards. Then, the manipulation part 50 may be manually moved upwards by the user.

Next, the ultrasonic wave generating unit 30 is moved upwards in conjunction with the upward movement of the variable shaft 40. As a result, the focusing depth of the ultrasonic waves of the transducer 32 becomes smaller.

Then, the locations of the movable shaft 121 and the second magnetic member 140 are fixed, but the second magnetic member 140 is magnetically coupled to a lower side of the first magnetic member 130 as the variable shaft 40 and the first magnetic member 130 are moved upwards.

Meanwhile, when the variable shaft 40 is moved upwards, the movable shaft 121 is fixed but the variable shaft 40 is moved upwardly. Accordingly, the second magnetic member 140 may be coupled to a lower side of the first magnetic member 130 while the first magnetic member 130 provided in the variable shaft 40 is moved upwardly.

Furthermore, when the ultrasonic wave generating unit 30 is moved upwards, the pair of elastic members 80 elastically support the ultrasonic wave generating unit 30 whereby the ultrasonic wave generating unit 30 may be prevented from being pivoted.

Hereinafter, an operation example in which the ultrasonic wave generating unit 30 of the ultrasonic wave generating apparatus according to the first embodiment of the inventive concept is moved in the axial direction of the variable shaft 40 will be described.

Figure 5:
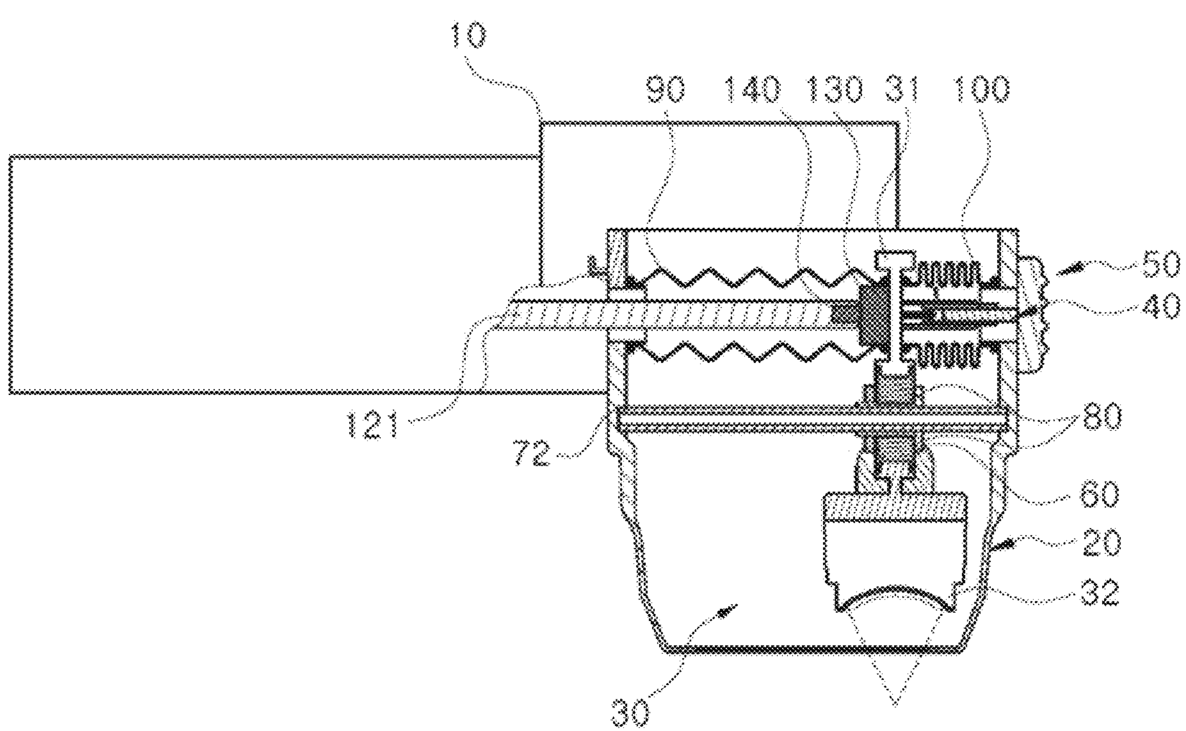
FIG. 5 is an operation view illustrating a state in which an ultrasonic wave generating unit of the ultrasonic wave generating apparatus according to the first embodiment of the inventive concept is moved.

FIG. 5 is an operation view illustrating a state, in which the ultrasonic wave generating unit of the ultrasonic wave generating apparatus according to the first embodiment of the inventive concept is moved in the axial direction of the variable shaft.

As illustrated in FIG. 5, first, the driving device moves the movable shaft 121 such that the movable shaft 121 approaches the manipulation part 50.

Next, as the movable shaft 121 is moved in a direction approaching the manipulation part 50, the connector 31 also is moved in a direction, approaching the manipulation part 50, and the ultrasonic wave generating unit 30 also is moved in a direction approaching the manipulation part 50 in conjunction therewith.

Meanwhile, when the variable shaft 40 is moved in a direction approaching the manipulation part 50, the first tube 90 is prolonged and the second tube 100 is compressed.

Furthermore, when the ultrasonic wave generating unit 30 is moved in a direction, in which the variable shaft 40 approaches the manipulation part 50, the bushing 60 provided in an interior of the ultrasonic wave generating unit 30 may be slid along the guide shaft 72.

Figure 6:
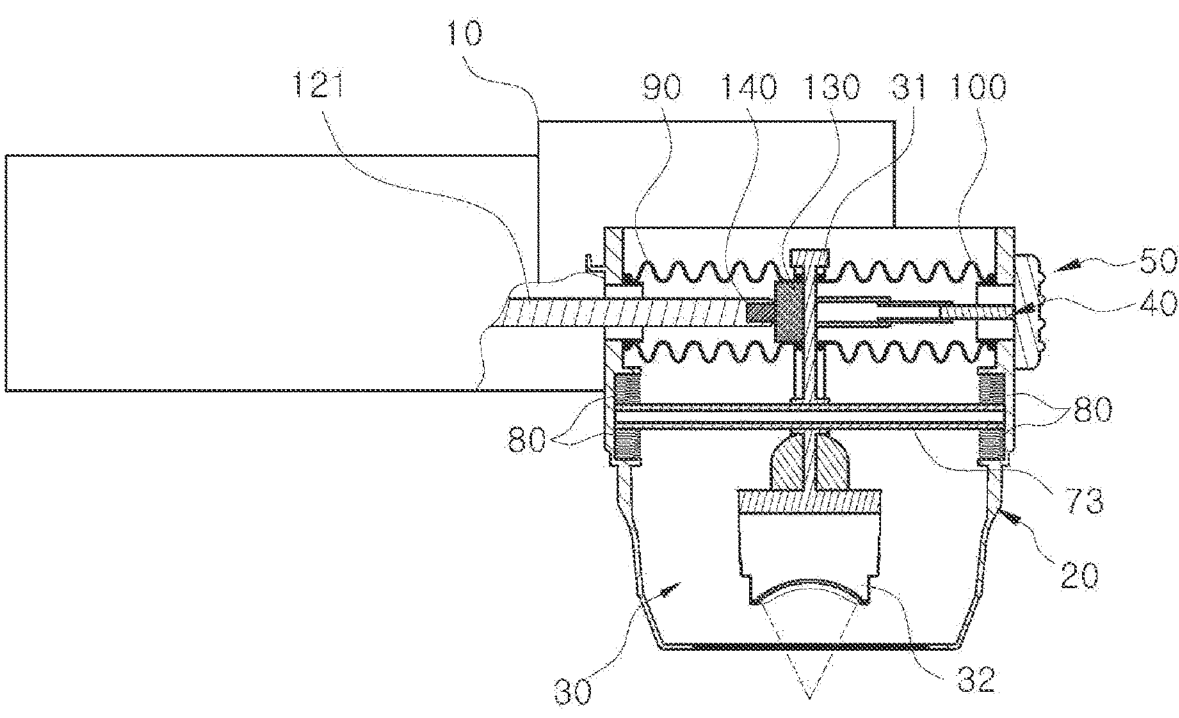
FIG. 6 is a schematic view illustrating an ultrasonic wave generating apparatus according to a second embodiment of the inventive concept.

FIG. 6 is a schematic view illustrating an ultrasonic wave generating apparatus according to a second embodiment of the inventive concept.

As illustrated in FIG. 6, unlike the first embodiment of the inventive concept, according to the ultrasonic wave generating apparatus according to the second embodiment of the inventive concept, a guide shaft 73 may be provided in the cartridge housing 20 to be coupled to the connector 31 of the ultrasonic wave generating unit 30, and may be moved in the upward/downward direction of the transducer 32 in conjunction with the variable shaft 40.

In other words, the guide shaft 73 may be moved in the upward/downward direction of the transducer 32, together with the variable shaft 40 and the ultrasonic wave generating unit 30.

In the embodiment, the pair of elastic members 80 may be disposed at ends of the guide shaft 73 to face each other, and may elastically support the guide shaft 73 that is moved in the upward/downward direction of the transducer 32. The pair of elastic members 80 may be provided at opposite sides of the guide shaft 73, respectively.

Hereinafter, an example of adjusting a focusing depth of ultrasonic waves of the transducer 32 of the ultrasonic wave generating apparatus according to the second embodiment of the inventive concept will be described. Hereinafter, for convenience of description, the upward/downward direction of the transducer 32 will be defined as an upward/downward direction.

Figure 7:
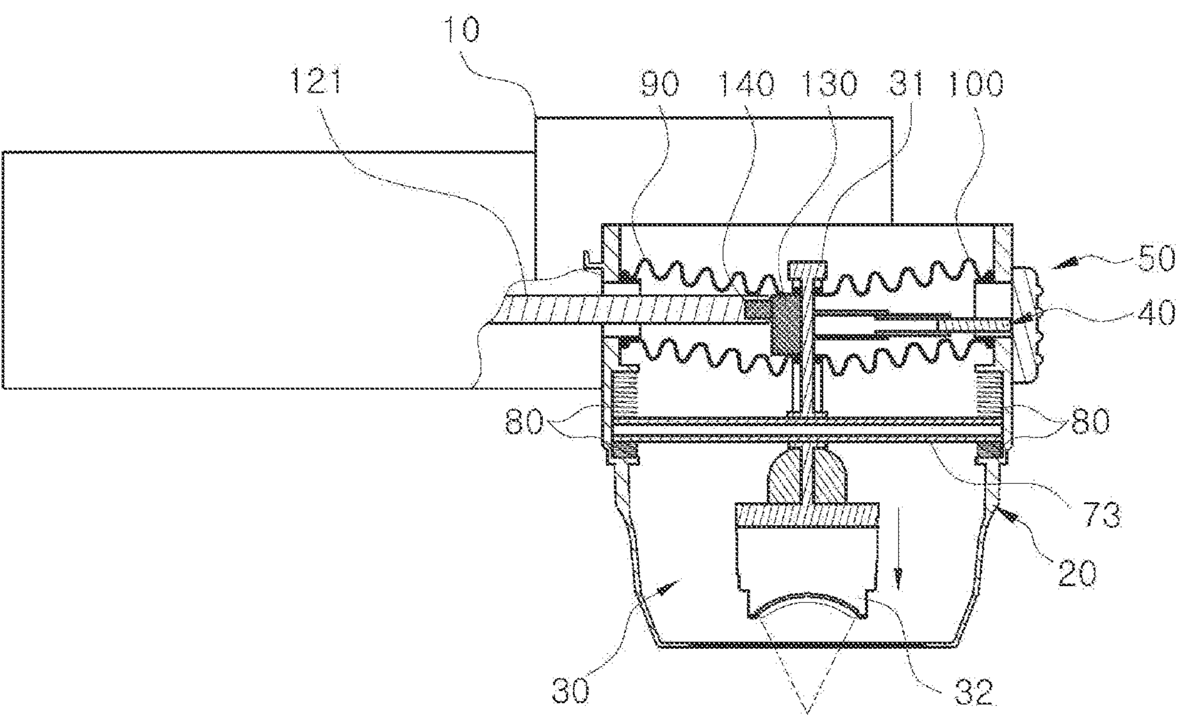
FIGS. 7 and 8 are operation views illustrating states, in which a focusing depth of ultrasonic waves of a transducer of the ultrasonic wave generating apparatus according to the second embodiment of the inventive concept is adjusted.
Figure 8:
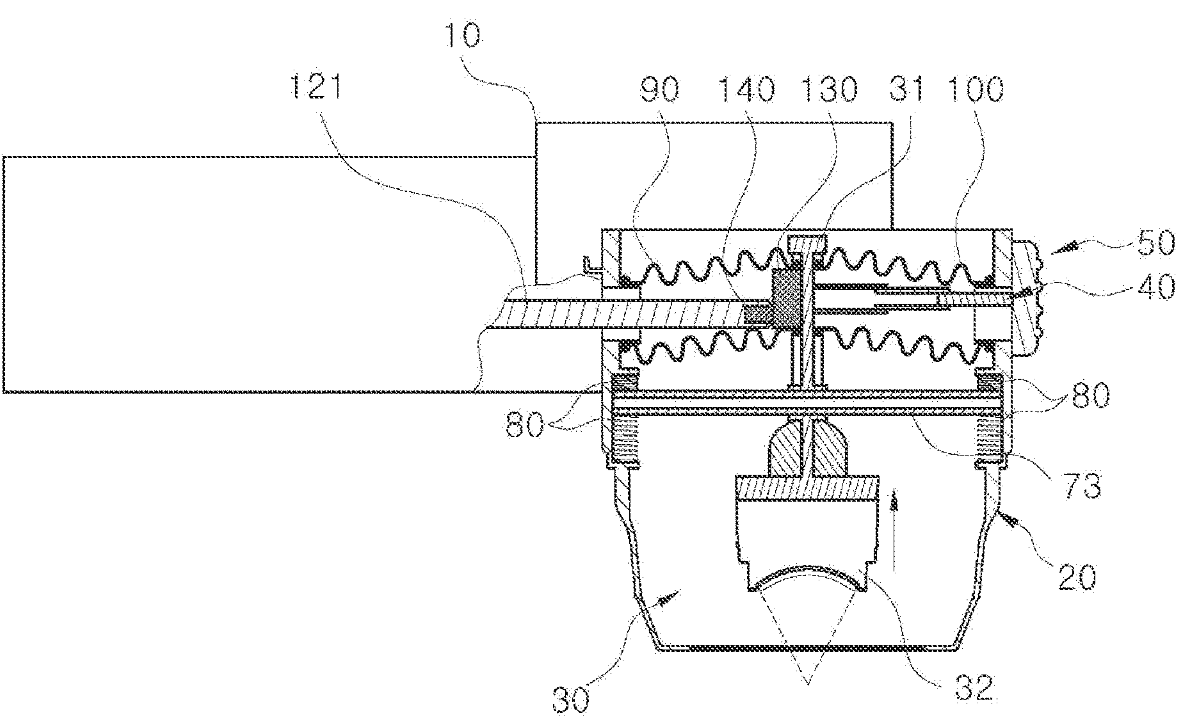

FIGS. 7 and 8 are operation views illustrating states, in which a focusing depth of ultrasonic waves of a transducer of the ultrasonic wave generating apparatus according to the second embodiment of the inventive concept is adjusted.

As illustrated in FIG. 7, first, the manipulation part 50 moves the variable shaft 40 downwards. Then, the manipulation part 50 may be moved downwards through manipulation by the user.

Next, the ultrasonic wave generating unit 30 and the guide shaft 73 also are moved downwards in conjunction with the downward movement of the variable shaft 40. As a result, the focusing depth of the ultrasonic waves of the transducer 32 becomes larger.

Meanwhile, when the variable shaft 40 is moved downwardly, the movable shaft 121 is fixed but the variable shaft 40 is moved downwardly. Accordingly, the second magnetic member 140 may be coupled to an upper side of the first magnetic member 130 while the first magnetic member 130 provided on the variable shaft 40 is moved downwardly.

Furthermore, when the ultrasonic wave generating unit 30 is moved downwards, the pair of elastic members 80 elastically support the guide shaft 73 that is moved in conjunction with the ultrasonic wave generating unit 30 whereby the ultrasonic wave generating unit 30 may be prevented from being pivoted.

Subsequently, as illustrated in FIG. 8, first, the manipulation part 50 moves the variable shaft 40 upwards. Then, the manipulation unit 50 may be manually moved upwards by the user.

Next, the ultrasonic wave generating unit 30 and the guide shaft 73 also are moved upwards in conjunction with the upward movement of the variable shaft 40. As a result, the focusing depth of the ultrasonic waves of the transducer 32 becomes smaller.

Meanwhile, when the variable shaft 40 is moved upwardly, the movable shaft 121 is fixed but the variable shaft 40 is moved upwardly. Accordingly, the second magnetic member 140 may be coupled to a lower side of the first magnetic member 130 while the first magnetic member 130 provided on the variable shaft 40 is moved upwardly.

Furthermore, when the ultrasonic wave generating unit 30 is moved upwards, the pair of elastic members 80 elastically support the guide shaft 73 that is moved in conjunction with the ultrasonic wave generating unit 30 whereby the ultrasonic wave generating unit 30 may be prevented from being pivoted.

Meanwhile, an ultrasonic wave generating cartridge according to the inventive concept is detachably mounted on the handpiece 10, and may include the cartridge housing 20, the ultrasonic wave generating unit 30, the variable shaft 40, the manipulation part 50, the guide part, and the elastic member 80.

Furthermore, the ultrasonic wave generating cartridge according to the inventive concept may further include the movable shaft 121, the first magnetic member 130, and the second magnetic member 140.

According to the inventive concept, the ultrasonic wave generating apparatus according to an embodiment of the inventive concept may easily adjust the focusing depth of the ultrasonic waves according to the target depth of skin.

The ultrasonic wave generating apparatus according to an embodiment of the inventive concept may easily adjust a focusing depth of ultrasonic waves according to a target depth of skin.

Furthermore, according to the ultrasonic wave generating apparatus according to an embodiment of the inventive concept, because the connector of the ultrasonic wave generating unit is coupled to the guide shaft to be slid, the ultrasonic wave generating unit is prevented from being pivoted while the ultrasonic wave generating unit is moved along the upward/downward direction or is moved along the axial direction of the variable shaft when the location of the ultrasonic wave generating unit is adjusted whereby the location of the ultrasonic wave generating unit may be easily adjusted and an ultrasonic wave treatment may be stably performed through the transducer of the ultrasonic wave generating unit while the location of the ultrasonic wave generating unit is precisely adjusted.

The effects of the inventive concept are not limited to the above-mentioned ones, and the unmentioned effects will be clearly understood by an ordinary person in the art from the following description.

Although the embodiments of the inventive concept have been described with reference to the attached drawings until now, an ordinary person in the art, to which the inventive concept pertains, may understand that the inventive concept may be carried out in other detailed forms without changing the technical spirits or the essential features. Therefore, it should be understood that the above-described embodiments are exemplary in all aspects and are not restrictive.

What is claimed is:

1. An ultrasonic wave generating apparatus capable of adjusting a focusing depth of ultrasonic waves, the ultrasonic wave generating apparatus comprising:

a handpiece;

a cartridge housing;

an ultrasonic wave generator provided in the cartridge housing, connected to a first shaft extending from the handpiece, and including a transducer configured to generate the ultrasonic waves;

a second shaft connected to the ultrasonic wave generator, wherein the second shaft has an adjustable axial length along a longitudinal axis thereof;

an actuator configured to move the transducer upwards and downwards in a direction perpendicular to the longitudinal axis of the second shaft, wherein upward movement corresponds to movement away from a patient and downward movement corresponds to movement closer to the patient; and a third shaft fixed to the cartridge housing and configured to guide the upward and downward movement of the transducer and to guide axial movement of the second shaft along the longitudinal axis of the second shaft, the third shaft comprising a bushing slidably disposed thereon;

wherein the first shaft is configured to be movable in an axial direction of the second shaft;

wherein the ultrasonic wave generator further includes a pair of elastic members configured to support the bushing, and wherein the pair of elastic members includes a first elastic member disposed above the third shaft and a second elastic member disposed below the third shaft, wherein the first elastic member contracts and the second elastic member elongates in response to the downward movement of the transducer, and the first elastic member elongates and the second elastic member contracts in response to the upward movement of the transducer.

2. The ultrasonic wave generating apparatus of claim 1, wherein movement of the first shaft in the axial direction of the second shaft is configured to adjust the axial length of the second shaft.

3. The ultrasonic wave generating apparatus of claim 1, wherein the second shaft is a telescopic shaft, and wherein the axial length of the second shaft is adjustable in a telescopic manner.

4. The ultrasonic wave generating apparatus of claim 1, wherein the third shaft is a guide shaft passing through the ultrasonic wave generator.

5. The ultrasonic wave generating apparatus of claim 1, further comprising:

a first magnetic member provided in the ultrasonic wave generator; and a second magnetic member provided in the first shaft and magnetically coupled to the first magnetic member.

6. The ultrasonic wave generating apparatus of claim 1, wherein the actuator comprises a driver, a button, or a knob.

7. An ultrasonic wave generating apparatus capable of adjusting a focusing depth of ultrasonic waves, the ultrasonic wave generating apparatus comprising:

a handpiece;

a cartridge housing;

an ultrasonic wave generator provided in the cartridge housing, connected to a first shaft extending from the handpiece, and including a transducer configured to generate the ultrasonic waves;

a second shaft connected to the ultrasonic wave generator, wherein the second shaft has an adjustable axial length along a longitudinal axis thereof; and an actuator configured to move the transducer upwards and downwards in a direction perpendicular to the longitudinal axis of the second shaft, wherein upward movement corresponds to movement away from a patient and downward movement corresponds to movement closer to the patient; and a third shaft fixed to the cartridge housing and configured to guide the upward and downward movement of the transducer and to guide axial movement of the second shaft along the longitudinal axis of the second shaft, the third shaft comprising a bushing slidably disposed thereon;

wherein the first shaft is configured to be movable in an axial direction of the second shaft;

wherein the ultrasonic wave generator further includes a pair of elastic members configured to support the third shaft, and wherein the pair of elastic members includes a first elastic member disposed above the third shaft and a second elastic member disposed below the third shaft, wherein the first elastic member contracts and the second elastic member elongates in response to the downward movement of the transducer, and the first elastic member elongates and the second elastic member contracts in response to the upward movement of the transducer.

8. The ultrasonic wave generating apparatus of claim 7, wherein movement of the first shaft in the axial direction of the second shaft is configured to adjust the axial length of the second shaft.

9. The ultrasonic wave generating apparatus of claim 7, wherein the second shaft is a telescopic shaft, and wherein the axial length of the second shaft is adjustable in a telescopic manner.

10. The ultrasonic wave generating apparatus of claim 7, wherein the third shaft is a guide shaft passing through the ultrasonic wave generator.

11. The ultrasonic wave generating apparatus of claim 7, further comprising:

a first magnetic member provided in the ultrasonic wave generator; and a second magnetic member provided in the first shaft and magnetically coupled to the first magnetic member.

12. The ultrasonic wave generating apparatus of claim 7, wherein the actuator comprises a driver, a button, or a knob.

13. An ultrasonic wave generating apparatus with an adjustable ultrasonic wave focal depth, the ultrasonic wave generating apparatus comprising:

a handpiece;

a first shaft extending from the handpiece;

a cartridge housing;

an ultrasonic wave generator provided in the cartridge housing and connected to the first shaft, the ultrasonic wave generator including a transducer operable to generate ultrasonic waves;

a second shaft connected to the ultrasonic wave generator, wherein the second shaft has an adjustable axial length;

an actuator operable to move the second shaft and the transducer of the ultrasonic wave generator in a retraction direction an extension direction, the retraction and extension directions being perpendicular to a longitudinal axis of the second shaft; and a guide shaft passing through the ultrasonic wave generator:

wherein the first shaft is configured to be movable in an axial direction corresponding to the longitudinal axis of the second shaft;

wherein the ultrasonic wave generator further includes a pair of elastic members, wherein the pair of elastic members are coupled with the guide shaft or a bushing configured to slide over the guide shaft, and the pair of elastic members are disposed to face each other in the retraction direction or the extension direction, with the guide shaft or the bushing interposed between the pair of elastic members, and wherein the pair of elastic members elastically support the guide shaft or the bushing in response to movement of the second shaft and the transducer in the extension direction, and in response to movement of the second shaft and the transducer in the retraction direction.

14. The ultrasonic wave generating apparatus of claim 13, wherein movement of the first shaft in the axial direction adjust the axial length of the second shaft.

15. The ultrasonic wave generating apparatus of claim 13, wherein the second shaft is a telescopic shaft, and wherein the axial length of the second shaft is adjustable in a telescopic manner.

16. The ultrasonic wave generating apparatus of claim 13, further comprising:

a first magnetic member provided in the ultrasonic wave generator; and a second magnetic member provided in the first shaft and magnetically coupled to the first magnetic member.

17. The ultrasonic wave generating apparatus of claim 13, wherein the actuator comprises a driver, a button, or a knob.

18. An ultrasonic wave generating apparatus capable of adjusting a focusing depth of ultrasonic waves, the ultrasonic wave generating apparatus comprising:

a handpiece comprising a movable shaft;

a cartridge housing;

an ultrasonic wave generator disposed in the cartridge housing, connected to the movable shaft, and comprising a pair of elastic members and a transducer configured to generate the ultrasonic waves;

a variable shaft having a longitudinal axis, the variable shaft being coupled to the ultrasonic wave generator and having an adjustable axial length along the longitudinal axis, the movable shaft being movable in an axial direction of the variable shaft;

an actuator operable to move the transducer in a first direction and a second direction that are each perpendicular to the longitudinal axis of the variable shaft; and a guide shaft disposed between the pair of elastic members and configured to guide movement of the transducer in the first and second directions and to guide axial movement of the variable shaft along the longitudinal axis of the variable shaft, the pair of elastic members being disposed to face each other in the first direction or the second direction so as to elastically support the guide shaft in response to movement of the transducer in the first direction, and in response to movement of the transducer in the second direction.

* * * * *